United States Patent
Jay et al.

(10) Patent No.: US 7,711,403 B2
(45) Date of Patent: May 4, 2010

(54) NON-INVASIVE DETERMINATION OF BLOOD COMPONENTS

(75) Inventors: Gregory D. Jay, Norfolk, MA (US); Selim Suner, North Kingstown, RI (US); Kevin S. Ernsting, Mountain View, CA (US)

(73) Assignee: Rhode Island Hospital, Providence, RI (US)

( * ) Notice: Subject to any disclaimer, the term of this patent is extended or adjusted under 35 U.S.C. 154(b) by 853 days.

(21) Appl. No.: 10/116,258

(22) Filed: Apr. 4, 2002

(65) Prior Publication Data

US 2003/0002722 A1    Jan. 2, 2003

Related U.S. Application Data

(60) Provisional application No. 60/281,941, filed on Apr. 5, 2001.

(51) Int. Cl.
*A61B 5/00* (2006.01)

(52) U.S. Cl. .................. 600/407; 600/473; 600/474; 600/476; 600/477; 600/558; 600/310; 600/316; 600/322; 600/368; 356/456

(58) Field of Classification Search .......... 600/407, 600/473, 474, 476, 477, 558, 310, 316, 322, 600/368; 356/456
See application file for complete search history.

(56) References Cited

U.S. PATENT DOCUMENTS

| | | | | |
|---|---|---|---|---|
| 3,743,429 | A |  7/1973 | Kawai | 356/180 |
| 4,914,512 | A |  4/1990 | Sekiguchi | 358/98 |
| 4,998,533 | A * |  3/1991 | Winkelman | 600/368 |
| 5,018,531 | A |  5/1991 | Hartman | 128/774 |
| 5,132,826 | A |  7/1992 | Johnson et al. | 359/93 |
| 5,348,003 | A |  9/1994 | Caro | 128/633 |
| 5,741,213 | A * |  4/1998 | Kouchi et al. | 600/310 |
| 5,750,994 | A |  5/1998 | Schlager | 250/339 |

(Continued)

FOREIGN PATENT DOCUMENTS

DE    31 37 326 A1    3/1983

(Continued)

OTHER PUBLICATIONS

International Search Report mailed Dec. 9, 2002.

(Continued)

*Primary Examiner*—Brian Casler
*Assistant Examiner*—Baisakhi Roy
(74) *Attorney, Agent, or Firm*—Mintz, Levin, Cohn, Ferris, Glovsky and Popeo, PC (57) ABSTRACT

A method of estimating an amount of a substance in a bodily fluid from the color of a tissue surface of a subject includes capturing an image including at least a portion-of-interest of the subject and at least a reference portion of a color reference, the image being a digital image of pixels of at least one color, the image including a component value for each pixel for each of the at least one color, obtaining a first value associated with at least one component value corresponding to the portion-of-interest of the subject, obtaining a second value associated with at least one component value corresponding to the reference portion, and calculating an estimated amount of the substance using the first and second values.

25 Claims, 7 Drawing Sheets

U.S. PATENT DOCUMENTS

| | | | | |
|---|---|---|---|---|
| 5,791,345 | A | 8/1998 | Ishihara et al. | 128/637 |
| 5,836,872 | A * | 11/1998 | Kenet et al. | 600/306 |
| 5,842,979 | A | 12/1998 | Jarman | 600/322 |
| 6,198,532 | B1 * | 3/2001 | Cabib et al. | 356/456 |
| 6,494,576 | B1 * | 12/2002 | L'Esperance, Jr. | 351/206 |
| 6,544,193 | B2 * | 4/2003 | Abreu | 600/558 |
| 6,567,573 | B1 | 5/2003 | Domash et al. | 385/16 |
| 6,587,701 | B1 * | 7/2003 | Stranc et al. | 600/310 |
| 6,751,490 | B2 * | 6/2004 | Esenaliev et al. | 600/310 |
| 2002/0131694 | A1 | 9/2002 | So et al. | 385/27 |
| 2003/0048970 | A1 | 3/2003 | Cole et al. | 385/1 |
| 2003/0050541 | A1 | 3/2003 | Wuori | 600/316 |
| 2004/0024295 | A1 * | 2/2004 | Cook et al. | 600/310 |
| 2004/0136581 | A1 * | 7/2004 | Ellis et al. | 382/128 |
| 2004/0156016 | A1 | 8/2004 | Kerr et al. | 351/206 |

FOREIGN PATENT DOCUMENTS

| | | |
|---|---|---|
| DE | 197 41 198 A1 | 6/1998 |
| JP | 7-213512 | 8/1995 |
| JP | 9-159606 | 6/1997 |
| JP | HEI10-210324 | 8/1998 |
| JP | 10-262957 | 10/1998 |
| JP | 2000-35702 | 12/2000 |
| JP | 2001-33381 | 2/2001 |
| JP | 2001-517521 | 10/2001 |
| JP | 2002-543863 | 12/2002 |
| WO | 99/16353 | 4/1999 |
| WO | 00/67635 | 11/2000 |
| WO | WO 01/20406 A1 | 3/2001 |
| WO | WO 01/56463 A1 | 8/2001 |
| WO | WO 02/060321 A2 | 8/2002 |

OTHER PUBLICATIONS

Hung et al., "Evaluation of the physician's ability to Recognize the Presence of Absence of Anemia, Fever, and Jaundice", *Academic Emergency Medicine*, 7(2):146-156 (2000).

Nagpal et al., "The Conjunctival Sickling Sign, Hemoglobin S, and Irreversibly Sickled Erythrocytes", *Arch. Ophthalmol.*, 95:808-811 (1977).

Sanchez-Carrillo, C.I., "Bias Due to Conjunctiva Hue and the Clinical Assessment of Anemia", *J. Clin. Epidemiol.*, 42(8):751-754 (1989).

Sanchez-Carrillo, et al., "Test of a Noninvasive instrument for measuring Hemoglobin Concentration", *Intl. J. Technol. Assess. Health Care*, 5:659-667 (1989).

Strobach et al., "The Value of the Physical Examination in the Diagnosis of Anemia", *Arch. Intern. Med.*, 148(4):831-832 (1988).

* cited by examiner

NON-INVASIVE DETERMINATION OF BLOOD COMPONENTS

CROSS-REFERENCE TO RELATED ACTIONS

This application claims the benefit of U.S. Provisional Application No. 60/281,941 filed Apr. 5, 2001.

FIELD OF THE INVENTION

The invention relates to determining hemoglobin concentrations and more particularly to determining hemoglobin concentrations in a non-invasive manner.

BACKGROUND OF THE INVENTION

Determining hemoglobin (Hb) concentrations is often useful in diagnosis and treatment of patients. For example, Hb concentrations are useful in diagnosing whether a person is anemic. Several techniques currently exist for determining serum hemoglobin. For example, techniques include phlebotomy (puncturing a vein and drawing blood) with subsequent laboratory analysis of the drawn blood, microscopic assessment of mucous membranes, and subjective assessment of conjunctiva color and clinical parameters. By far the most widely used technique is phlebotomy followed by analysis with a flow cytometer. This technique is reliable, but uses one or more technicians, an expensive piece of equipment (the cytometer), and typically a centralized location for the analysis due to the cost of the cytometer. Another technique uses magnification and analysis of blood flow through mucous membranes.

SUMMARY OF THE INVENTION

In general, in an aspect, the invention provides a method of estimating an amount of a substance in a bodily fluid from the color of a tissue surface of a subject. The method includes capturing an image including at least a portion-of-interest of the subject and at least a reference portion of a color reference, the image being a digital image of pixels of at least one color, the image including a component value for each pixel for each of the at least one color, obtaining a first value associated with at least one component value corresponding to the portion-of-interest of the subject, obtaining a second value associated with at least one component value corresponding to the reference portion, and calculating an estimated amount of the substance using the first and second values.

Implementations of the invention may include one or more of the following features. The image comprises a plurality of colors for each pixel, wherein obtaining the first value comprises obtaining a plurality of first values each associated with at least one component value of a corresponding color, wherein obtaining the second value comprises obtaining a plurality of second values each associated with at least one component value of a corresponding color, and wherein the calculating the estimated amount uses each of the plurality of first and second values. The obtaining the first and second values comprises averaging component values in a first portion of the portion-of-interest and a second portion of the reference portion, respectively, for each of the plurality of colors. The calculating comprises using first and second empirically-predetermined weighting constants associated with the first and second values respectively.

Implementations of the invention may also include one or more of the following features. The method further includes selecting a first portion of the portion-of-interest and a second portion of the color reference, and wherein the first and second values are obtained from at least one component value of each of the first and second portions, respectively. The first portion is a biologically perfused surface of the subject. The capturing is performed non-invasively.

Implementations of the invention may also include one or more of the following features. The capturing, the obtaining a first value, the obtaining a second value, and the calculating are preformed in real time. The obtaining a first value, the obtaining a second value, and the calculating are at least partially performed by a processor executing software instructions. The portion-of-interest is a conjunctiva and the amount of the substance is a hemoglobin concentration. The method further includes displaying the estimated amount. The estimated amount is a hemoglobin concentration and is displayed in units of grams per deciliter (g/dl).

In general, in another aspect, the invention provides a method of determining factors that influence estimation of an amount of a substance in a bodily fluid from the color of a tissue surface of a subject. The method includes capturing an image including at least a portion-of-interest of the subject and at least a reference portion of a color reference, the image being a digital image of pixels of at least one color, the image including a component value for each pixel for each of the at least one color, establishing a first factor associated with the portion-of-interest and a second factor associated with the reference portion, calculating an estimated amount of the substance in the subject using the component values and the first and second factors, comparing the estimated amount with a corresponding known amount of the substance in the subject, and adjusting, if the estimated amount has other than a desired relationship with the known amount, at least one of the first and second factors.

Implementations of the invention may include one or more of the following features. The method further includes repeating the calculating, the comparing, and the adjusting until the estimated amount of the substance has the desired relationship with the known amount of the substance. The method further includes storing the first and second factors when the estimated amount of the substance has the desired relationship with the known amount of the substance. The image comprises a plurality of colors for each pixel, wherein the establishing establishes a plurality of first factors and a plurality of second factors each corresponding to a respective one of the plurality of colors, wherein the calculating the estimated amount uses each of the first and second factors, and wherein the adjusting adjusts any of the first and second factors. The method further includes selecting a first region of the portion-of-interest and a second region of the reference color. The calculating uses averages of the component values for each color over the first and second regions, respectively. The calculating uses ratios of the averages of the component values for each color over the first and second regions, respectively.

In general, in another aspect, the invention provides a system for determining a level of a substance in a bodily fluid from the color of a tissue surface. The system includes a color separator module configured to decompose a digital color image of a perfused surface of a subject and a color reference object into sub-images of component colors, the sub-images comprising digital component values corresponding to pixels of the image, a portion selector module in communication with the color separator module and configured to select a first window of the image of the perfused surface and to select a second window of the image of the color reference object, and a substance estimator module in communication with the portion selector and configured to calculate an estimated level of the substance using window values associated with component values corresponding to the first and second windows.

Implementations of the invention may include one or more of the following features. The system further includes an imaging module configured to capture the image and to convey the digital component values of the image to the color separator module. The imaging module is configured to capture the image non-invasively. The portion selector module is further configured to average the component values of each sub-image to produce the window values, with one window value for each sub image for each of the first and second windows. The color separator module, the portion selector module, and the substance estimator module each comprise computer-executable instructions, stored on a computer-readable medium, for causing a computer to perform actions as recited in claim 20. The system further includes a display coupled to the substance estimator module and configured to display indicia of the estimated level of the substance.

Various aspects of the invention may provide one or more of the following advantages. Hemoglobin concentrations are determined regardless of lighting conditions, in real-time, at remote locations, and with inexpensive equipment. Hemoglobin concentrations are determined objectively, reliably, and repeatably. Hemoglobin concentrations are determined using, e.g., a portable digital camera including specialized software. Hemoglobin concentrations are determined non-invasively and using widely available resources.

These and other advantages of the invention, along with the invention itself, will be more fully understood after a review of the following figures, detailed description, and claims.

DETAILED DESCRIPTION OF PREFERRED EMBODIMENTS

The invention provides techniques for determining the concentration of a substance in bodily fluids such as blood for diagnostic purposes. For example, the methods are useful to determine the concentration of hemoglobin, methemoglobin, carboxyhemoglobin, bilirubin, and bile salts to determine whether an individual is suffering from or at risk of developing a pathological condition such as anemia, dyshemoglobinemia, methemoglobinemia, carboxyhemoglobinemia, and carbon monoxide poisoning. Bilirubin disorders such as hyperbilirubinemia and bilirubinuria are also diagnosed using the methods described herein.

In accordance with the invention, a user digitally photographs a patient and a gray reference simultaneously and adjacently. The digitally-captured image is processed based on known relationships of images and the gray reference with known hemoglobin concentrations or concentrations of other blood components. From the processing, a hemoglobin concentration figure is produced. This figure can be used to diagnose hemoglobin-related health issues (or at least health issues for which hemoglobin concentrations are indicated). For example, hemoglobin levels outside a normal range (14-18 g/dL for human male subjects; 12-16 g/dL for human female subjects) or bilirubin concentrations outside a normal range (0.3-1.0 mg/dL) indicate a pathological condition or a risk of developing such a condition.

Figure 1:
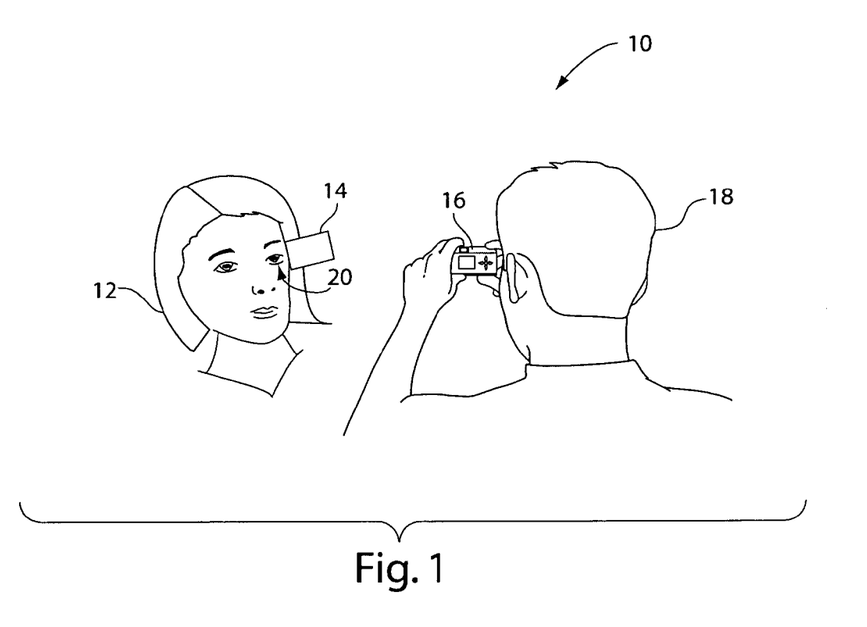
FIG. 1 is a schematic perspective view of a system for estimating biologically-relevant factors.

Referring to FIG. 1, a system 10 includes a subject 12, a gray-reference card 14, a digital camera 16, and a user 18. The subject is a person whose hemoglobin concentration is to be determined. The gray-reference card 14 is a known shade of gray, here an 18% photographic standard gray card (i.e., the card is 18% of the way from pure white to pure black). The card 14 is disposed adjacent an area 20 of the subject 12 to be imaged. Preferably, the area 20 is a biologically perfused surface that's color is influenced by the subject's blood. For example, the area 20 can be, e.g., the subject's conjunctiva, a mucous membrane, nail bed, earlobe, skin, lips, or retina. The camera 16 is a digital camera configured to be manipulated by the user 18 to obtain a digital image of the area 20 of the subject 12. The camera 16 images the area 20 as a set of pixels with red, green, and blue components with corresponding red, green, and blue values for each pixel. Here, the camera 16 can resolve the level of red, green, and/or blue for any given pixel into one of 256 different shades, yielding a composite image of over 16 million colors (256*256*256). The camera 16 is configured with computer-executable software to process levels of red, green, and blue of the area 20 as compared to the card 14 as described below to determine a hemoglobin concentration of the subject 12. The camera 16 includes a display screen for displaying estimated hemoglobin concentrations in units of grams per deciliter (g/dl).

Figure 2:
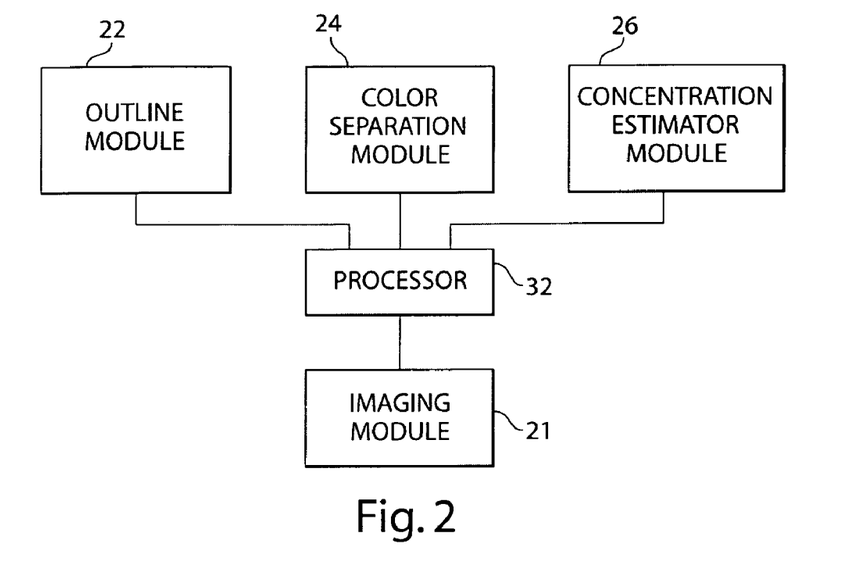
FIG. 2 is a block diagram of modules of a digital camera shown in FIG. 1.

Referring also to FIG. 2, the digital camera 16 includes an imaging module 21, an outlining software module 22, a color separation software module 24, and a hemoglobin concentration estimator software module 26. Each of the modules 22, 24, 26 includes computer-executable instructions stored on a computer-readable medium such that the instructions can be read and executed by a processor 32 of the camera 16. The modules may be referred to as performing actions as shorthand for the processor 32 executing the modules' instructions for performing the listed actions/functions. The imaging module 21 includes both hardware and software. The imaging module 21 is configured to cause the camera 16 to take pictures and capture color images, the images being composed of pixels of red, blue, and green components having respective red, blue, and green component digital values.

Figure 3:
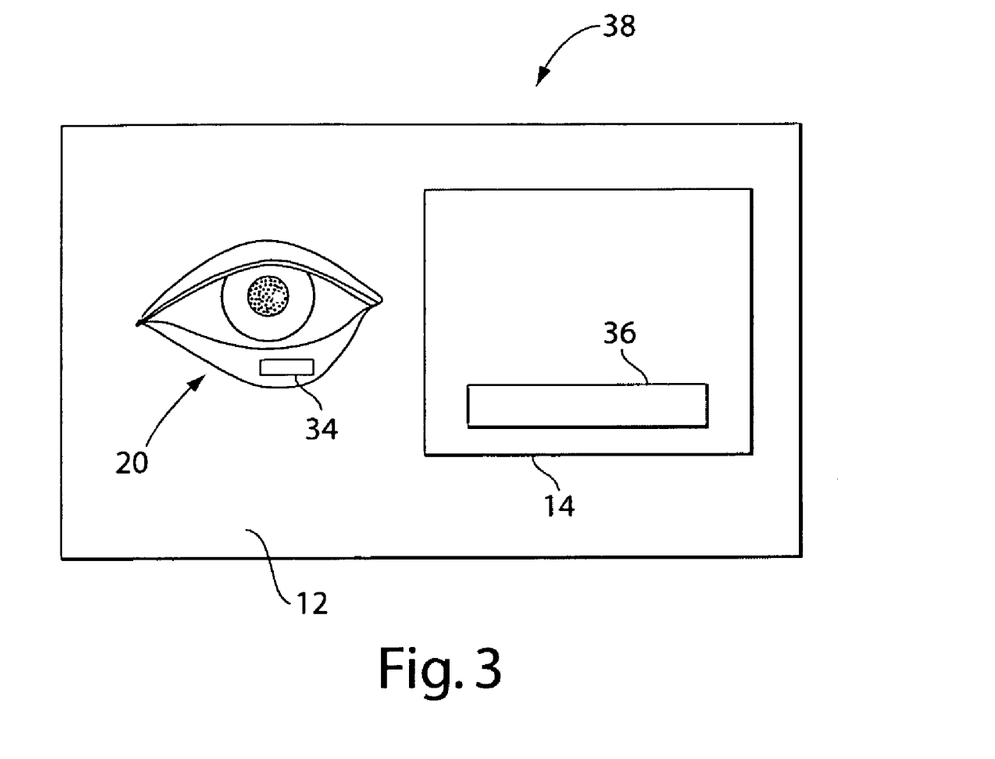
FIG. 3 is a simplified diagram of an image, taken using the camera shown in FIG. 1, including a portion of a subject and a color-reference card.

The outlining module 22 is configured to select portions of an image corresponding to the area 20 of the subject 12, and the card 14. As shown in FIG. 3, the outlining module can select or outline a window 34 in the region 20 of the subject 12, and a window 36 of the card 14, from an image 38 taken by the camera 16. As shown, the region 20 is the conjunctiva, of the subject 12, that has been exposed by turning down the lower eyelid of the subject 12.

The color separation module 24 is configured to use imaging software, e.g., available from the National Institute of Health (NH) (NIH Image for MacIntosh computers and Scion Image for PCs; information is available at NIH's Web page). The module 24 uses the imaging software to separate or deconstruct the colors imaged by the camera 16 into the components of the pixels forming the image 38. Thus, three sub-images similar to those shown in FIG. 3 are produced, one in red, one in green, and one in blue. The module 24 is further configured to average the digital component values over the outlined regions 34, 36 and to determine ratios of average component values for red, green, and blue of the window 34 of the subject 12 and of the window 36 of the gray-reference card 14.

The estimator module 26 is configured to use ratios of values of the separated colors relative to the card 14 from the color separation module 24, along with predetermined weighting constants, as inputs to formulas that produce a hemoglobin estimate. The estimator module 26 is configured to select measured values from the imaging module 24 corresponding to different selected portions of the image 38 taken by the camera 16 and to use the selected measured values to determine the hemoglobin concentration estimate. Specifically, the estimator module 26 is configured to determine a hemoglobin estimate $Hb_{est}$ according to:

$$Hb_{est}=1.15*((hgb+hgb1)/2) \quad (1)$$

where $$hgb1=(120-((bme_c-gme_c)+(120-(gme_c-rme_c)-20)-20))/12 \quad (2)$$

and $$hgb=(40+((160-(((bme_c-gme_c)+(140-(gme_c-rme_c))-12)))/4))/4.5 \quad (3)$$

$$bmult=150/bme_s \quad (4)$$

$$gmult=165/gme_s \quad (5)$$

$$rmult0.8+(130/rme_s) \quad (6)$$

where $bme_s$, $gme_s$, and $rme_s$ are the means (averages) of the blue, green, and red, respectively, component values for the pixels in the window 36 of the reference card 14 used as a standard, and where $bme_c$, $gme_c$, and $rme_c$ are the means (averages) of the blue, green, and red, respectively, component values for the pixels in the window 34 of the area 20, here the subject's conjunctiva, multiplied by bmult, gmult, and rmult, respectively. Thus, $bme_c$, $gme_c$, and $rme_c$ include ratios of the averages of the component values in the window 34 and the averages of the component values in the window 36. The constants, i.e., 150 in equation (4), 165 in equation (5), and 0.8 and 130 in equation (6) are weighting constants empirically determined as described below.

Figure 4:
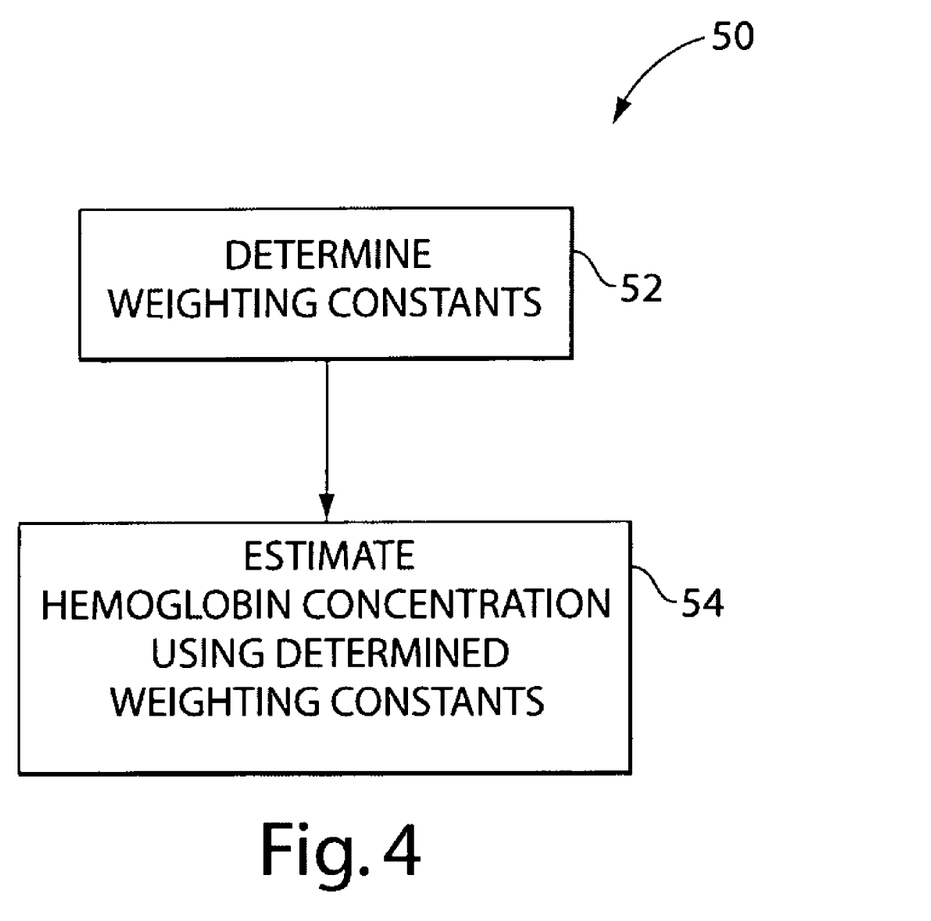
FIG. 4 is a block flow diagram of a process of estimating hemoglobin concentration.

In operation, referring to FIG. 4, with further reference to FIGS. 1-3, a process 50 for estimating the subject's hemoglobin concentration using the camera 16 includes the stages shown. The process 50, however, is exemplary only and not limiting. The process 50 can be altered, e.g., by having stages added, removed, or rearranged. The process 50 includes a stage 52 where weighting constants are determined, and a stage 54 where the determined weighting constants are applied to an image of a subject to estimate the subject's hemoglobin.

Figure 5:
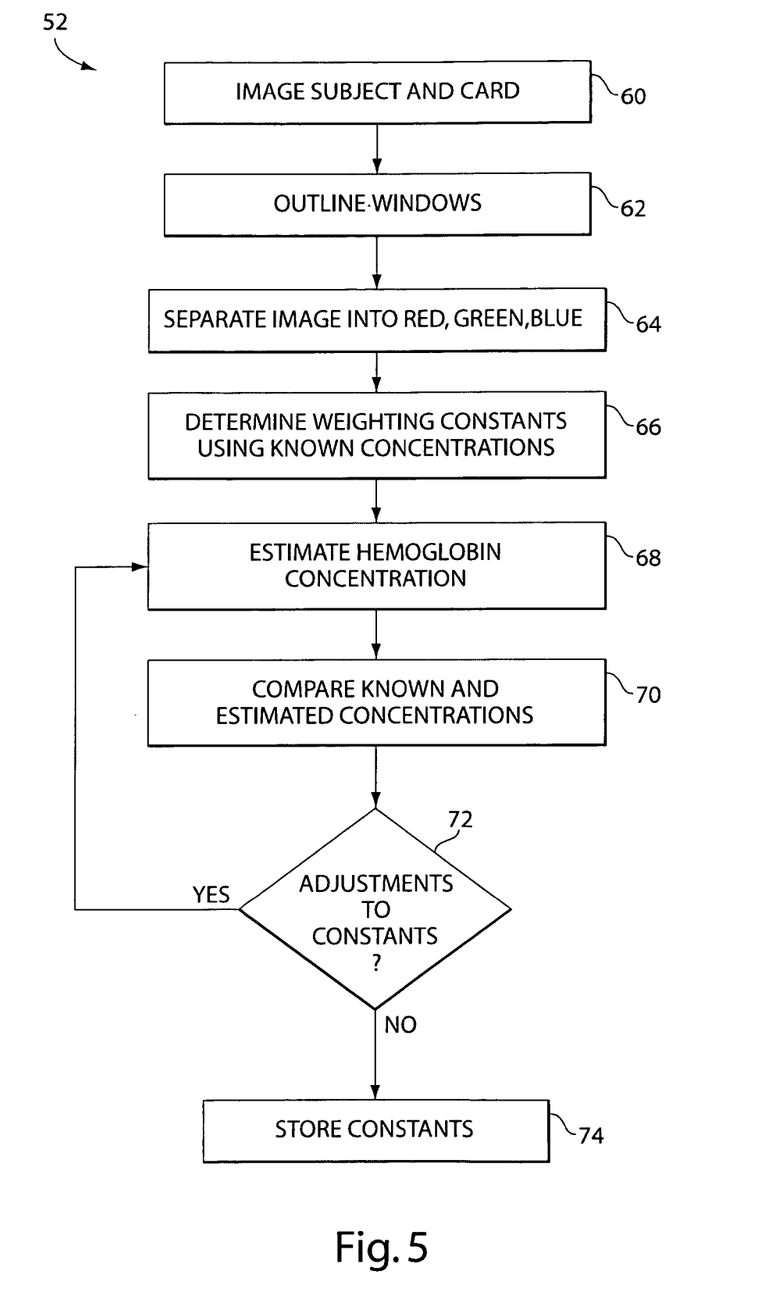
FIG. 5 is a block flow diagram of a process of determining weighting constants for estimating hemoglobin concentration.

Referring also to FIG. 5, stage 52 of the process 50 includes the stages shown for determining the weighting constants to be used at stage 54. The stages shown are exemplary only and not limiting. Stages may be added, removed, or rearranged.

At stage 60, the image 38 of the subject 12 and the card 14 is taken using the camera 16. The card 14 is placed adjacent the region 20 to be imaged, here the subject's conjunctiva. The subject 12 everts the subject's lower eyelid and holds the card 14 adjacent to the subject's head at eye level. The user 18 actuates the camera 16 to take the image 38.

At stage 62, the windows 34, 36 of the subject 12 and the card 14 are outlined. The outline module 22 outlines the windows 34, 36 in the region 20 of the subject 12 and within the perimeter of the card 14

At stage 64, the image 38 is separated into red, green, and blue images. The color separation module 24 separates the pixels of the image 38 using the imaging software (e.g., NIH Image or Scion Image). The module 24 further determines ratios of red, green, and blue values to a value associated with the gray-reference card.

At stage 66, a weighting constant is determined for each color (red, green, and blue) using known hemoglobin concentrations. Values of ratios from stages 62, 64, and 66 for several subjects 12 are provided, along with a known hemoglobin concentrations of these same subjects 12 (e.g., derived from phlebotomy and laboratory analysis). The provided values are entered into equations (1)-(6) with initial red, green, and blue weighting constants. The initial constants are arbitrary, e.g., 1, but may be selected to help reduce the number of iterations involved in determining final weighting constants.

At stage 68, the subject's hemoglobin concentration is estimated by the concentration estimator module 26. The module 26 uses the values of the ratios from stage 66 in equations (1)-(6) to estimate the subject's hemoglobin concentration.

At stage 70, the estimated and known concentrations are compared. The estimated versus known hemoglobin concentrations are compared to determine whether adjustments to one or more of the weighting constants is appropriate (i.e., if the estimated and known concentrations meet or do not meet desired criteria such as being within a desired percentage of each other).

At stage 72, appropriate adjustments are made to the red, green, and/or blue weighting constants. The weighting constants are adjusted to attempt to achieve a more accurate hemoglobin concentration estimate. If any adjustment is made to a weighting constant, then the process 60 returns to stage 68 where the hemoglobin concentration for a particular subject 12 is determined. If no adjustments are made, then the process 60 proceeds to stage 74.

At stage 74, the weighting constants are stored for future use. The red, green, and blue weighting constants are stored for use in determining estimates of hemoglobin concentrations for subjects 12 whose hemoglobin may not be determined through other means, e.g., phlebotomy and lab analysis.

Figure 6:
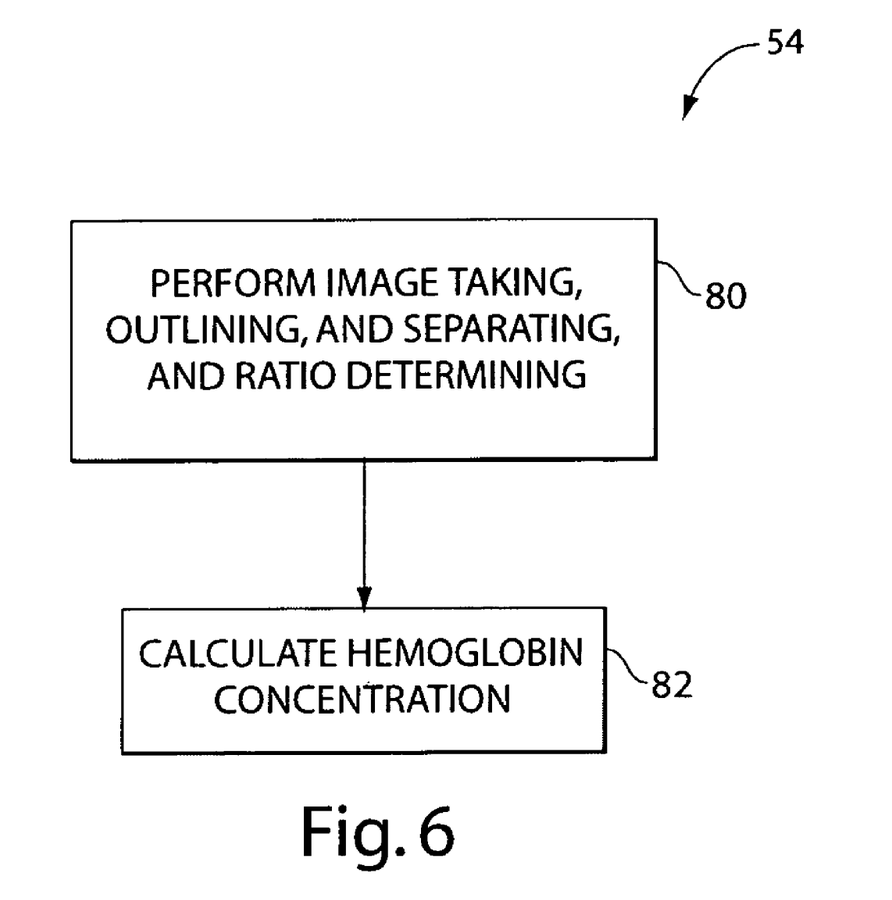
FIG. 6 is a block flow diagram of a process of estimating hemoglobin concentration using the weighting constants determined using the process shown in FIG. 5.

Stage 52 thus provides stage 54 with red, green, and blue weighting constants for use in estimating hemoglobin concentrations for other subjects 12. Referring also to FIG. 6, stage 54 of the process 50 includes the stages shown for using the determined the weighting constants to estimate the subject's hemoglobin concentration. The stages shown are exemplary only and not limiting. Stages may be added, removed, or rearranged.

At stage 80, stages 60, 62, and 64 shown in FIG. 5 are performed for a non-reference subject 12 whose hemoglobin concentration is to be estimated. Typically, this subject 12 will not have hemoglobin concentration determined through other means. The subject 12 may be located far away from other equipment needed for actual determination or direct measurement of hemoglobin concentration.

At stage 82, the ratios of color values to the gray card 14 determined at stage 80 are applied to estimate the subject's hemoglobin concentration. The concentration estimator module 26 uses the ratios provided from the color separation module 24 at stage 80 and the weighting constants determined in stage 52 in equations (1)-(3) to determine an estimation of the subject's hemoglobin concentration. The module 26 provides a number indicating the hemoglobin concentration upon which a diagnosis of the subject 12 may be based.

Stage 52 will typically occur well before stage 54, although this is not necessary. For example, the image 38 of the subject 12 may be taken at stage 80, then the weighting constant determined at stage 52, then the subject's hemoglobin estimated at stage 82. Further, after a hemoglobin concentration is estimated, weighting constants may be updated/refined and hemoglobin estimates recalculated.

Figure 7:
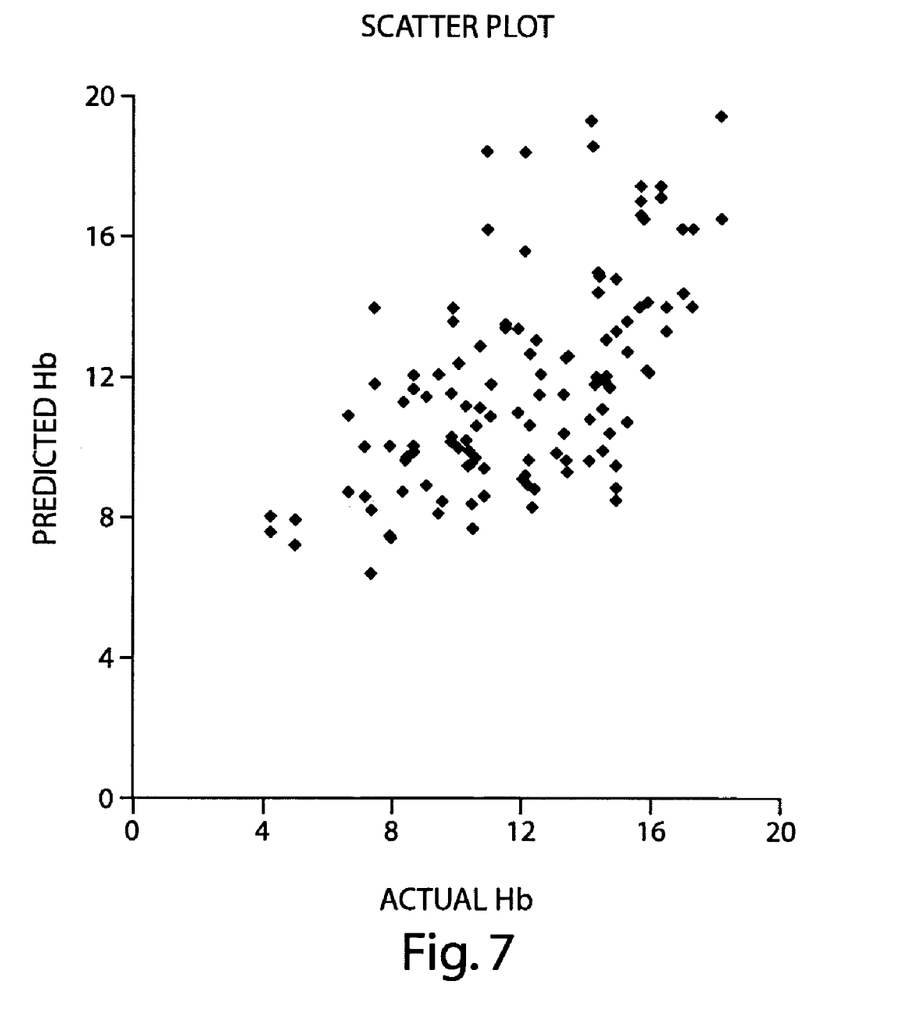
FIG. 7 is a scatter plot of experimental data showing predicted hemoglobin concentration, using the process shown in FIG. 5, and actual measured hemoglobin concentration. Hemoglobin is expressed as grams per deciliter (g/dL).

Referring to FIG. 7, experimental results using the process 50 evidenced a correlation between hemoglobin concentration and conjunctiva color. For the experiments, persons with active bleeding, oxygen saturation less than 90%, or a serum bilirubin over 3.0 mg/dL were excluded. Actual Hb was measured with a cell counter model SE9500 made by Sysmex Corp. of Kobe, Japan. Photographs were taken with a digital camera model DSC-F1, with 480×260 pixels, made by Sony Corp. of Tokyo, Japan. 117 images were used from 63 patients (79 images for formula derivation and 38 for a validation group). 46% of the patients were female, and the patients ranged in age from 20 to 87 years, with a mean 60±18. The formula derivation group had a Pearson's Rank Order Coefficient of $r(77)=0.634$, $p<0.01$. The validation group had a Pearson's Rank Order Coefficient of $r(36)=0.522$, $p<0.01$. The standard error was 2.57 and the standard deviation was 3.09.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. For example, portions of the software described above as being in the camera 16 can be disposed externally to the camera 16. One or more of the software modules may be disposed in an external computer, such as a laptop computer, or on a computer-readable medium such as a floppy disc or compact disc (including a re-writable compact disc). In these cases, images taken by the camera 16 can be loaded onto a computer that executes the software externally to the camera 16. The computer or other external device can display estimated amounts in appropriate units, such as hemoglobin concentrations in units of grams per deciliter (g/dl).

What is claimed is:

1. A non-invasive method of estimating an amount of hemoglobin in a bodily fluid from the color of a perfused tissue surface of a subject using a digital camera, the method comprising:
   non-invasively capturing, using the digital camera, a single image of light reflected from the perfused tissue surface of the subject and at least a reference portion of a known color reference simultaneously, the single image being a single image of pixels of a plurality of colors, the single image including red, green, and blue component values for each pixel wherein the perfused tissue surface of the subject is a conjunctiva of an eyelid;
   obtaining from the single image, using at least one processor in communication with the digital camera, red, green, and blue tissue values associated with the red, green, and blue component values, respectively, corresponding to a portion-of-interest of the single image of the perfused tissue surface of the subject;
   obtaining from the single image, using the at least one processor in communication with the digital camera, red, green, and blue reference values associated with the red, green, and blue component values, respectively, corresponding to the reference portion; and
   calculating, using the at least one processor in communication with the digital camera, an estimated hemoglobin concentration amount as a function of the red, green, and blue tissue values and the red, green, and blue reference values.

2. The method of claim 1 wherein obtaining the red, green, and blue tissue values and the red, green, and blue reference values comprises averaging component values in a first portion of the single image of the perfuse tissue surface and a second portion of the reference portion, respectively, for each of the red, green, and blue component values.

3. The method of claim 2 wherein the calculating comprises using first and second empirically-predetermined weighting constants associated with the red, green, and blue tissue values and the red, green, and blue reference values respectively.

4. The method of claim 1 further comprising selecting, using the at least one processor in communication with the digital camera, a first portion of the single image of the perfused tissue surface and a second portion of the color reference, wherein the red, green, blue tissue values are obtained from the first portion, and wherein the red, green, and blue reference values are obtained from the second portion.

5. The method of claim 1 wherein the capturing, the obtaining of red, green, and blue tissue values, the obtaining of the red, green, and blue reference values, and the calculating are performed in real time.

6. The method of claim 1 further comprising displaying, on a display in communication with the at least one processor, the estimated hemoglobin concentration amount.

7. The method of claim 6 wherein the estimated hemoglobin concentration amount is displayed in units of grams per deciliter (g/dl).

8. The method of claim 1 wherein capturing the single image includes capturing an image of the known color reference adjacent to the perfused tissue surface of the subject.

9. The method of claim 1 wherein capturing the single image includes capturing an image of a known color reference that is gray.

10. The method of claim 1 further comprising everting a lower eyelid of the subject to expose the conjunctiva of the eyelid.

11. A non-invasive method of determining factors that influence estimation of an amount of hemoglobin in a bodily fluid from the color of a perfused tissue surface of a subject, the method comprising:
    non-invasively capturing, using a digital camera, a single image of light reflected from the perfused tissue surface of the subject and at least a reference portion of a known color reference simultaneously, the single image including pixels of a plurality of colors, the single image including red, green, and blue component values for each pixel, wherein the perfused tissue surface of the subject is a conjunctiva of an eyelid;
    establishing, using at least one processor in communication with the digital camera, red, green, and blue tissue factors associated with a perfused tissue surface portion-of-interest of the single image of the subject, and red, green, and blue reference factors associated with the digital camera and a reference portion-of-interest of the single image of the subject;

calculating, using the at least one processor in communication with the digital camera, an estimated hemoglobin concentration amount using the single image and as a function of the red, green, and blue component values and the red, green and blue tissue factors, and the red, green, and blue reference factors;

comparing, using the at least one processor in communication with the digital camera, the estimated hemoglobin concentration amount with a corresponding known amount of hemoglobin in the subject; and adjusting, if the estimated hemoglobin concentration amount has other than a desired relationship with the known amount, at least one of the red, green, and blue tissue factors, and the red, green, and blue reference factors using the at least one processor in communication with the digital camera.

12. The method of claim 11 further comprising repeating the calculating, the comparing, and the adjusting until the estimated amount of hemoglobin has the desired relationship with the known amount of hemoglobin.

13. The method of claim 12 further comprising storing, in a memory in communication with the at least one processor, the red, green, and blue tissue factors and the red, green, and blue reference factors when the estimated amount of hemoglobin has the desired relationship with the known amount of hemoglobin.

14. The method of claim 11 further comprising selecting a first region of the single image of the perfused tissue surface and a second region of the reference color using the at least one processor in communication with the digital camera.

15. The method of claim 14 wherein the calculating uses averages of the red, green and blue component values for each color over the first and second regions, respectively.

16. The method of claim 15 wherein the calculating uses ratios of the averages of the red, green, and blue component values for each color over the first and second regions, respectively.

17. The method of claim 11 further comprising everting a lower eyelid of the subject to expose the conjunctiva of the eyelid.

18. A system for determining a level of hemoglobin in a bodily fluid from the color of a perfused tissue surface of a subject, the system comprising:

an imaging module configured to non-invasively capture a single color image of the perfused tissue surface of the subject and a known color reference object, wherein the perfused tissue surface is a conjunctiva of an eyelid;

a color separator module in communication with the imaging module and configured to decompose the single color image into sub-images of component colors, the sub-images comprising digital component values corresponding to pixels of the single image;

a portion selector module in communication with the color separator module and configured to select a first window of the single image of the perfused tissue surface and to select a second window of the single image of the color reference object; and a hemoglobin estimator module in communication with the portion selector and configured to calculate an estimated hemoglobin concentration level as a function of window values associated with component values corresponding to the first and second windows.

19. The system of claim 18 wherein the portion selector module is further configured to average the component values of each sub-image to produce the window values, with one window value for each sub image for each of the first and second windows.

20. The system of claim 18 wherein the color separator module, the portion selector module, and the hemoglobin estimator module each comprise computer-executable instructions, stored on a computer-readable medium, for causing a computer to perform actions as recited in claim 18.

21. The system of claim 18 further comprising a display coupled to the hemoglobin estimator module and configured to display indicia of the estimated hemoglobin level.

22. A non-invasive method of estimating a concentration of hemoglobin in blood of a subject from the color of a perfused tissue surface of the subject using a digital camera, the method comprising:

non-invasively capturing, using the digital camera, a single image of light reflected from the perfused tissue surface of the subject and at least a reference portion of a known color reference simultaneously, the single image being a single image of pixels a plurality of colors, the single image including red, green and blue component values for each pixel for each of the at least one color, wherein the perfused tissue surface of the subject is a conjunctiva of an eyelid;

obtaining from the single image, using at least one processor in communication with the digital camera, red, green, and blue tissue values associated with the red, green, and blue component values, respectively, corresponding to a portion-of-interest of the single image of the perfused tissue surface of the subject;

obtaining, from the single image, using the at least one processor in communication with the digital camera, red, green, and blue reference values associated with the red, green, and blue component values, respectively, corresponding to the reference portion; and calculating, using the at least one processor in communication with the digital camera, an estimated hemoglobin value indicative of a concentration of hemoglobin in the blood of the subject as a function of the red, green, and blue tissue values and the red, green, and blue reference values.

23. The method of claim 22 further comprising everting a lower eyelid of the subject to expose the conjunctiva of the eyelid.

24. A non-invasive method of determining factors that influence estimation of a concentration of hemoglobin in blood of a subject from the color of a perfused tissue surface of the subject, the method comprising:

non-invasively capturing, using a digital camera, a single image of light reflected from the perfused tissue surface of the subject and at least a reference portion of a known color reference simultaneously, the single image including pixels of a plurality of colors, the single image including red, green and blue component values for each pixel, wherein the perfused tissue surface of the subject is a conjunctiva of an eyelid;

establishing, using at least one processor in communication wiht the digital camera, red, green, and blue tissue factors associated with the digital camera and a tissue portion-of-interest of the single image of the subject, and red, green, and blue reference factors associated with the digital camera and a reference portion-of-interest of the single image of the subject;

calculating, using the at least one processor in communication with the digital camera, an estimated hemoglobin level, using the single image, that is indicative of a concentration of hemoglobin in the blood of the subject as a function of the red, green, and blue component values and the red, green, and blue tissue factors and the red, green, and blue reference factors;

comparing, using the at least one processor in communication with the digital camera, the estimated hemoglobin level with a corresponding known amount of hemoglobin in the subject; and adjusting, using the at least one processor in communication with the digital camera, if the estimated hemoglobin level has other than a desired relationship with the known amount, at least one of the red, green, and blue tissue factors and the red, green, and blue reference factors, respectively.

25. The method of claim 24 further comprising everting a lower eyelid of the subject to expose the conjunctiva of the eyelid.

* * * * *